United States Patent [19]
Latimer et al.

[11] Patent Number: 5,526,691
[45] Date of Patent: Jun. 18, 1996

[54] DETECTION OF CORROSION FATIGUE CRACKS IN MEMBRANE BOILER TUBES

[75] Inventors: Paul J. Latimer; Daniel T. Maclauchlan, both of Lynchburg, Va.

[73] Assignee: The Babcock & Wilcox Company, New Orleans, La.

[21] Appl. No.: 511,049

[22] Filed: Aug. 3, 1995

Related U.S. Application Data

[63] Continuation of Ser. No. 89,881, Jul. 12, 1993, abandoned.

[51] Int. Cl.⁶ .................................................. G01N 29/04
[52] U.S. Cl. ................................................ 73/592; 73/598
[58] Field of Search .............................. 73/592, 598, 599

[56] References Cited

U.S. PATENT DOCUMENTS

| | | | |
|---|---|---|---|
| 4,218,924 | 8/1980 | Fortunko et al. | 73/642 |
| 4,685,334 | 8/1987 | Latimer | 73/599 |
| 4,953,147 | 8/1990 | Cobb | 73/598 |
| 5,038,614 | 8/1991 | Bseisu et al. | 73/598 |

OTHER PUBLICATIONS

Power Engineering, May 1992, "A Vision for Reducing Boiler Tube Failures: Part II", Barry Dooly, Electric Power Research Institute.

*Primary Examiner*—Richard Chilcot
*Assistant Examiner*—Max Noori
*Attorney, Agent, or Firm*—Daniel S. Kalka; Robert J. Edwards

[57] ABSTRACT

A method for detecting corrosion fatigue cracks in membraned boiler tubes in a membrane tube panel employs at least one EMAT coil generating ultrasonic SH shear waves at a predetermined beam angle. The method of the present invention provides better signal-to-noise ratios than conventional ultrasonic techniques as well as not requiring any couplant.

5 Claims, 4 Drawing Sheets

5,526,691

DETECTION OF CORROSION FATIGUE CRACKS IN MEMBRANE BOILER TUBES

This is a continuation of application Ser. No. 08/089,881 filed Jul. 12, 1993 now abandoned.

BACKGROUND OF THE INVENTION

1. Field of the Invention

The present invention relates generally to a method for detecting corrosion fatigue cracks in membrane boiler tubes, and more particularly to a method for detecting corrosion fatigue cracks in membrane boiler tubes using EMATS.

2. Description of the Related Art

Corrosion fatigue is a form of failure mechanism found in boiler tubes in fossil fired utility boilers. The mechanism for corrosion fatigue results from the interaction of mechanical stress and corrosion. Cyclic stressing is more damaging than constant stress and as a result there are more failures of this type. The actual damage consists of crack initiation and growth from the water side surface (I.D.) of the boiler tube. Multiple cracking usually occurs with one crack dominating causing a through wall failure. Cracks are typically wide, oxide filled, and appear with an irregular bulge profile. The damage resulting from these cracks is particularly serious in universal pressure (UP) units which are also known as once-through boilers.

The crack growth usually is in a direction perpendicular to the maximum tensile stress and depending on the particular stress situation, stress assisted cracking may be longitudinal, circumferential, or occasionally inclined at some angle. Typically in the UP waterwall panels the cracking is longitudinal. The tubes in the waterwall panels of fossil units have cracks that are ID initiated, radially oriented, with the failures typically occurring at the membraned welds or 90° from the membrane welds on either the furnace side or the casing side.

In the past, if this problem was suspected in the utility boiler, the primary method of detection was radiography. Unfortunately, there are health hazards associated with radiography and due to the radiation large areas needed to be evacuated during inspection. Consequently, there have been various attempts to locate this type of damage by ultrasonic techniques. One conventional ultrasonic technique proved to be slow and thus could only serve as a survey technique for the high risk areas in the boiler. Even still, there were serious problems involved with poor signal-to-noise ratios evident on tubes with diameters smaller than 150 mills. A major problem associated with the ultrasonic test technique was that cracks can occur with equal probability on both the furnace and casing side of the membrane tube panel. The ultrasonic technique involved propagating ultrasound past the membrane which has a complex geometry. The other practical problem with the ultrasonic method is the size of the boiler tubes. Due to the small size of the tubes, there is very little room for an ultrasonic wedge.

Thus, there is a need for an alternate approach to inspecting boiler tubes for corrosion fatigue. The method should be rapid with much better signal-to-noise ratios then the conventional ultrasonic technique.

SUMMARY OF THE INVENTION

The present invention solves the aforementioned problems with the prior art as well as others by providing a method for detecting corrosion fatigue cracks in membrane boiler tubes using electromagnetic acoustic transducers (EMATS). SH shear waves are generated for inspection of the boiler tubes and the SH shear waves undergo no mode conversion upon successive bounces. Also, the beam angle is easily controllable with adjustment of the frequency.

Accordingly, an object of the present invention is to provide a method for detecting corrosion fatigue cracks in membraned boiler tubes using EMATS.

Another object of the present invention is to provide a method which requires no couplant with better signal to noise ratios then the conventional ultrasonic technique.

Still another object of the present invention is to provide a method which utilizes SH shear waves that undergo no mode conversion upon successive bounces. Still a further object of the present invention is to provide a method that is reliable, rapid, and economical.

The various features of novelty which characterize the present invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENT

Figure 1:
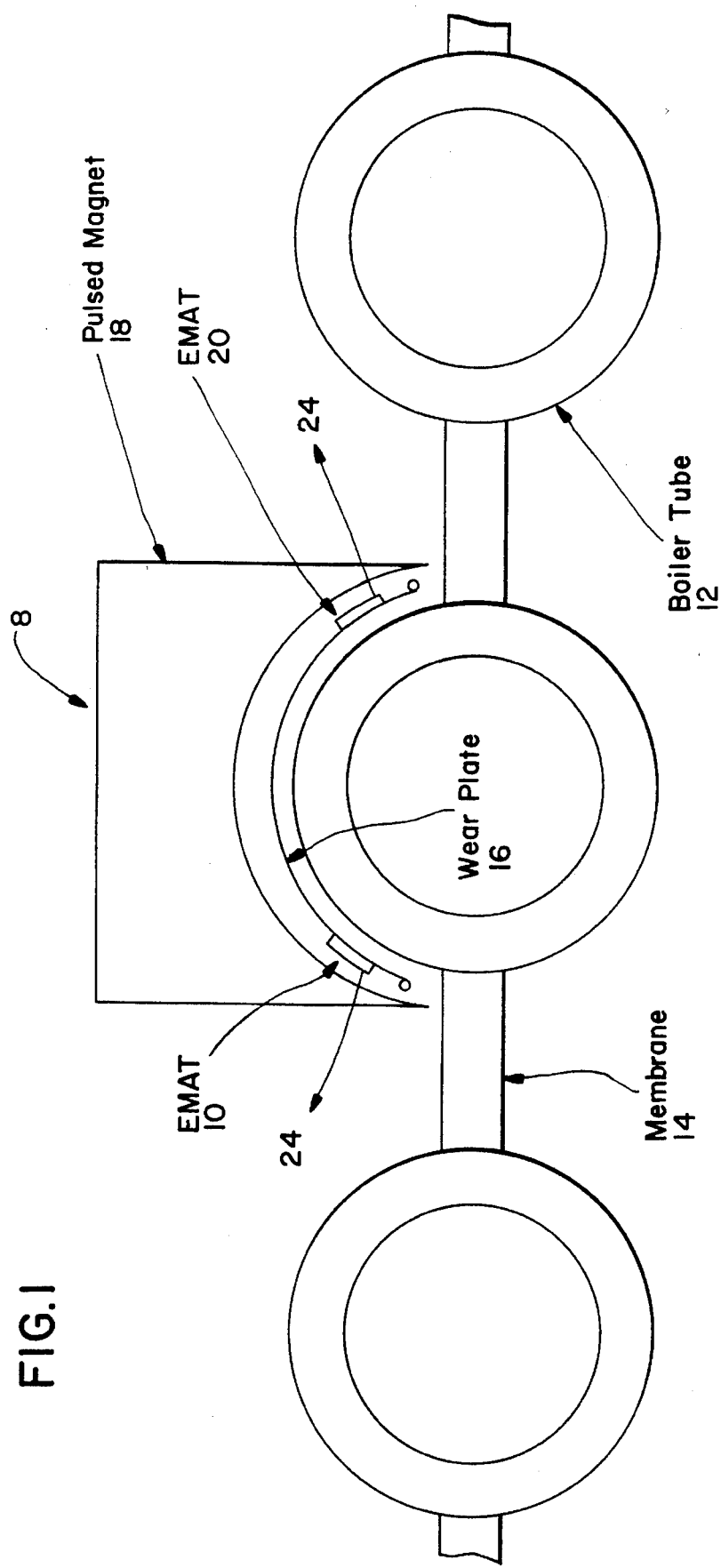
FIG. 1 is a schematic illustration of a cross-sectional view of one embodiment of the present invention in place on a portion of a membrane tube panel.

Referring to the drawings where like numerals designate like features throughout the several views, and first to FIG. 1, there is shown two EMAT coils (10, 20) positioned on a boiler tube (12). Boiler tube (12) is part of a membrane tube panel (14) well known in this art. The EMAT coils (10, 20) consist of two meander coils with a separation of adjacent conductors with a spacing that varies from 0.030" to 0.060". One suitable example contains five adjacent loops to an individual coil with the dimensions of the coil being 5/16" by 5/8". The EMAT coils (10, 20) are positioned at approximately 120°–170° on the adjacent membrane panel (14) as shown in FIG. 1. With this arrangement, any two EMAT coils can be used in a pitch-catch mode or any single EMAT coil can be used in a pulse-echo mode. The EMAT coils (10, 20) are protected by a wear plate (16) such as a titanium wear plate shown in FIG. 1 positioned adjacent the boiler tube (12). Alternatively, the EMAT coils (10, 20) may be covered with a suitable wear-resistant material such a polyethylene tape or thin titanium.

The EMAT coils (10, 20) and wear plate (16) along with a pulsed magnet (18) which is an electromagnet make up the EMAT transducer assembly (8). The pulsed magnet (18) is contained within a suitable fixture along with the other components of transducer (8). The pulsed magnet (18) supplies the magnetic field necessary for this method. Scanning of the boiler tube (12) on the membrane panel (14) is accomplished either mechanically with a mechanical scanner (not shown) or manually.

The orientation of the sensors is such that the magnetic field lines are parallel to the EMAT conductor. Other angles between EMAT and conductors may be used.

Figure 2:
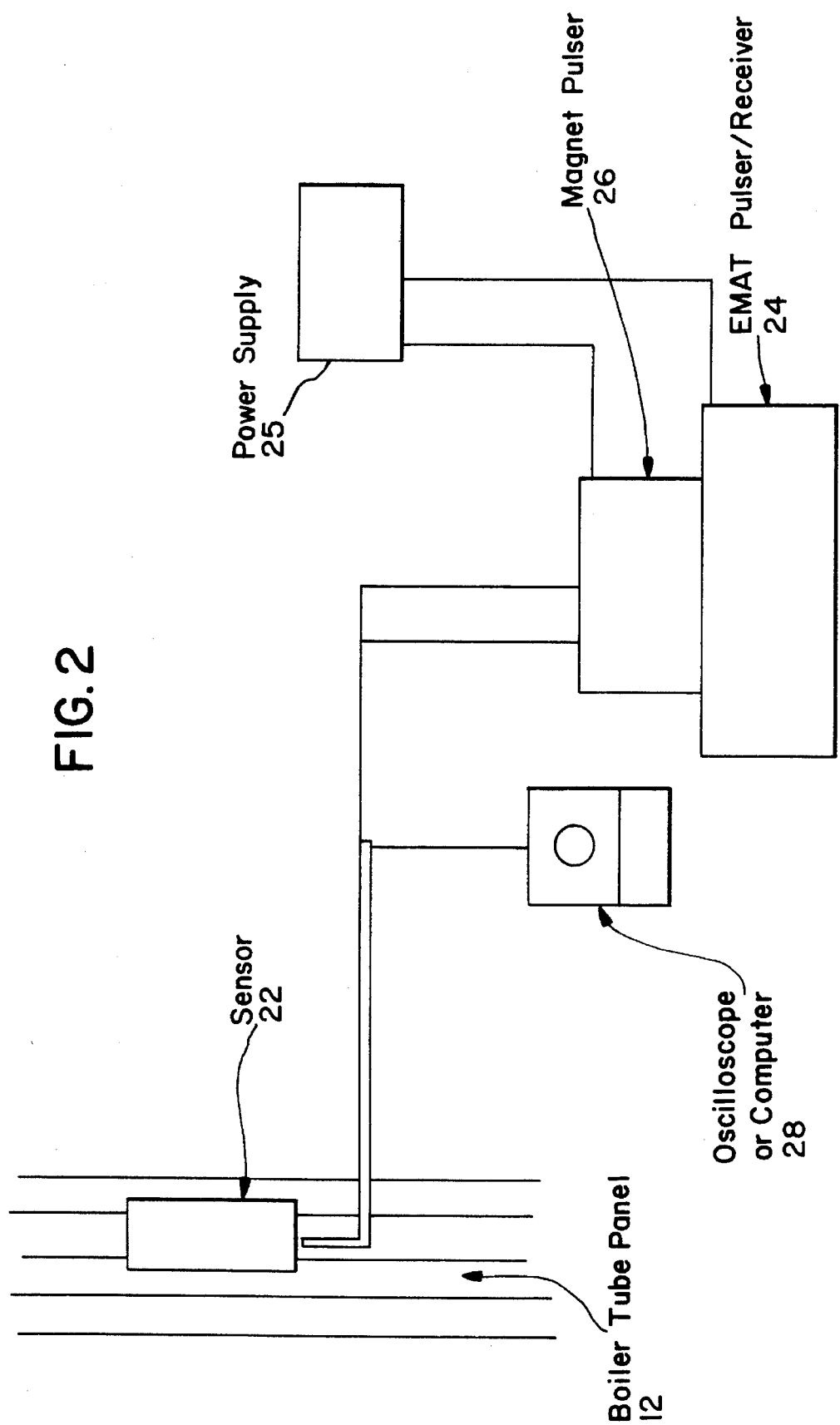
FIG. 2 is a schematic illustration of another embodiment of the present invention used to inspect the boiler tube panel.

Since the EMAT coils (10, 20) are bidirectional, an alternate embodiment uses one EMAT coil (10) to avoid crosstalk between the two sensors operating in a pulse-echo mode. FIG. 2 shows an alternate embodiment where the single sensor EMAT coil (22) is used to scan the boiler tube (12). The two sensor coils are used alternately in a pulse-echo mode to cover different portions of, the tube. For example, the area under sensor 1 cannot be inspected without sensor 2 and vice versa. An EMAT pulser-receiver (24) operated by power supply (not shown) receives the propagated ultrasonic waves and displays them on an oscilloscope or computer (28). The magnet pulser (26) along with sensor (22) generates the SH shear waves for inspecting the boiler tube (12). For the embodiment shown in FIG. 1, the EMAT data acquisition instrumentation (24, 28) is provided with two channels for the two EMAT coils (10, 20) which generate the SH shear waves. The EMAT coils (10, 20) are connected to a computer or oscilloscope (28) which receives the signals therefrom. Data acquisition by the oscilloscope or computer (28) is performed in at least two different modes. Either the wave forms and windows are displayed directly, or the peak amplitude in each window is displayed.

Figure 3:
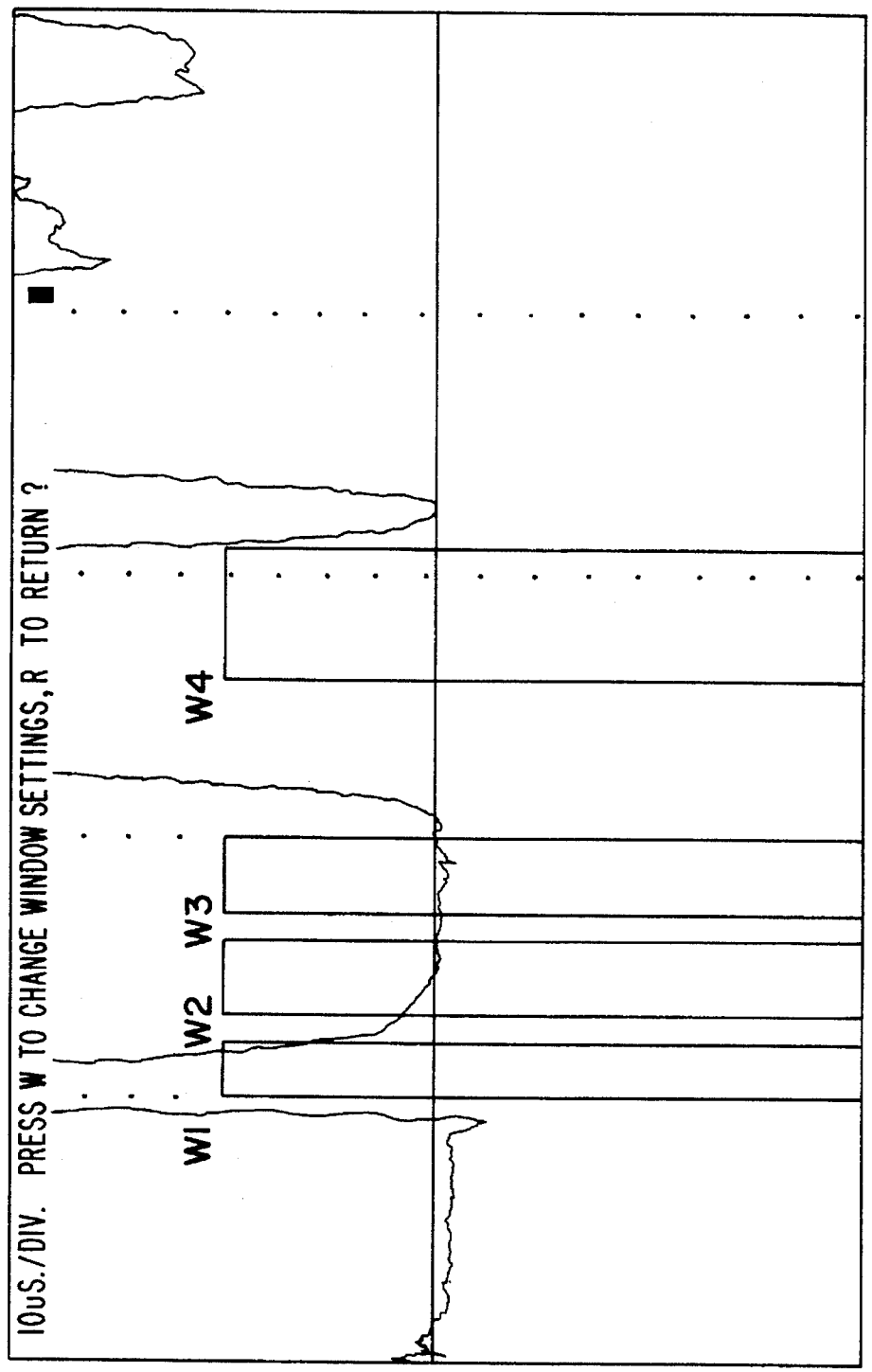
FIG. 3 is a plot from a computer showing one complete transit.
Figure 4:
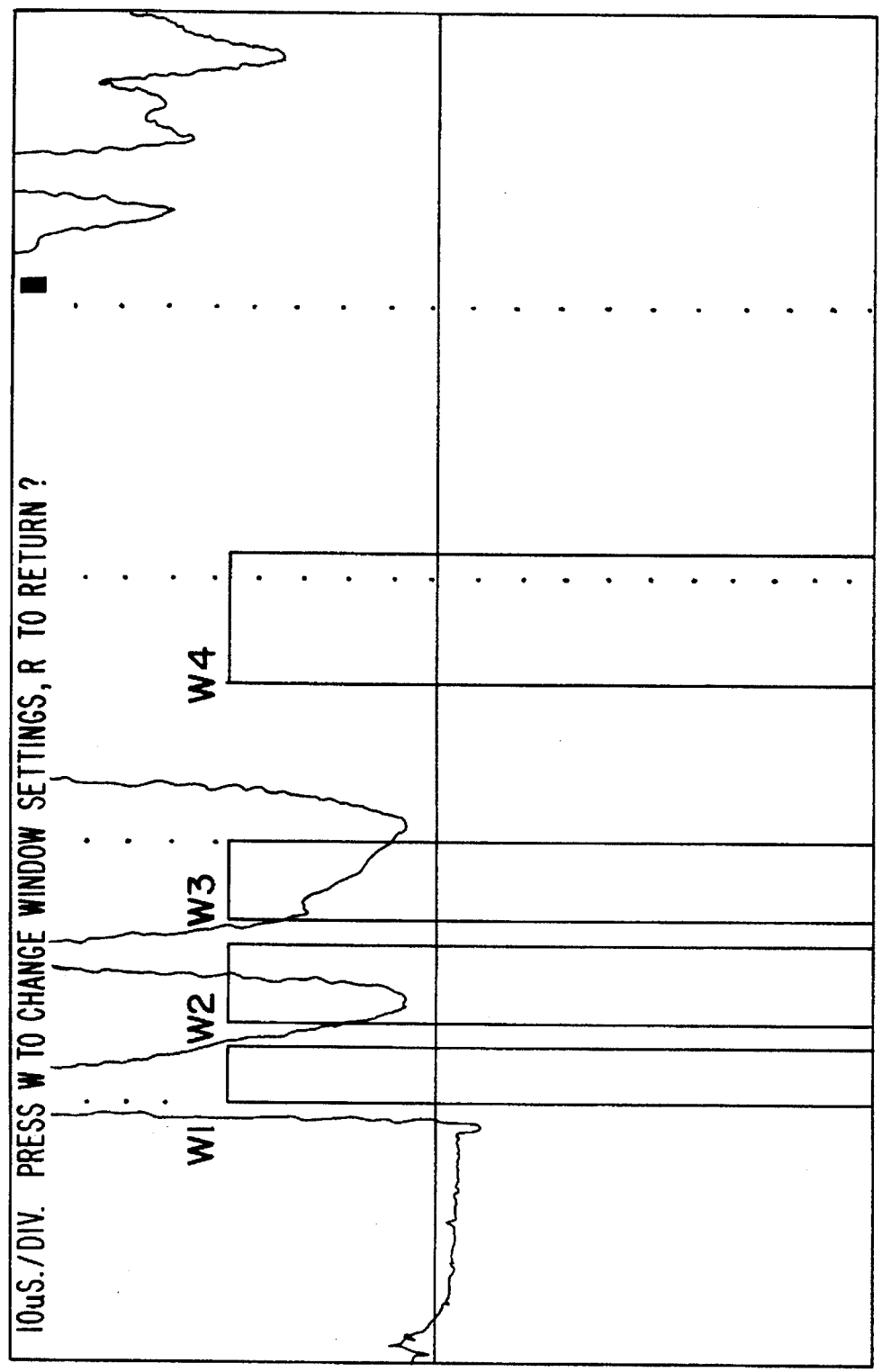
FIG. 4 is a view similar to FIG. 3 showing the detection of a natural flaw.

FIGS. 3 and 4 show the data acquisition display in four windows. The first window (W1) was set at the start of the initial pulse excitation. The fourth window (W4) was set at the position of one complete transit around the boiler tube (12). FIG. 4 at the third window (W3) shows the signal from a natural flaw. This signal is located between (W1) and (W4) and it is not known whether the flaw is located on the furnace side or the casing side due to the bi-directional nature of the EMAT coils (10, 20). The vertical dotted lines on the display represents ten used intervals in time. These results were obtained with boiler tubes having an outer diameter (O.D.) of 1.25 inch.

The beam angle is critical for a given tube diameter and wall thickness. The relationship between the beam angle and the frequency is given by the following formula:

$$\sin \Theta = c/2Df$$

where:

f=frequency c=shear wave velocity

D=separation between adjacent conductors in the EMAT coil

In practice, the correct angle is determined by examining a calibration standard with machined notches simulating the I.D. cracks.

Replaceable EMATS are required for different tube diameters. The signal-to-noise ratio is much better on tubes when the oxide coating is left intact. This is probably due to the magnetostrictive properties of the oxide coating.

As one example of the method of the present invention the preferred beam angle into steel is 52.9° when operating with a frequency of 2.63 MHz. Because of the tube outer diameter curvature, this is not the angle at which the SH shear waves intersect the flaw. It has been found for boiler tubes with a 1.25 inch OD, the optimum frequency is between about 2.63 MHz and 2.75 MHz. This angle will be different for each combination of tube diameter and wall thickness.

While specific embodiments of the invention have been shown and described in detail to illustrate the application of the principles of the invention, it will be understood that the invention may be embodied otherwise without departing from such principles.

What is claimed is:

1. A method for detecting corrosion fatigue cracks in boiler tubes, comprising the steps of:

positioning two electromagnetic acoustic transducers externally on a boiler tube of a boiler tube membrane tube panel, one electromagnetic acoustic transducer being positioned at approximately 120° and the other at approximately 170° adjacent the boiler tube;

generating ultrasonic SH shear waves with at least one of said electromagnetic acoustic transducers;

propagating the ultrasonic SH shear waves into the boiler tube at a predetermined beam angle with an adjustable frequency with the ultrasonic SH shear waves undergoing no mode conversion upon successive bounces as the ultrasonic SH shear waves propagate around the boiler tube;

measuring the returned ultrasonic SH shear waves from the boiler tube with at least one of said electromagnetic acoustic transducers; and determining from the returned ultrasonic SH shear waves any corrosion fatigue cracks with data acquisition means.

2. A method as recited in claim 1, further comprising the step of scanning the boiler tube for corrosion fatigue cracks.

3. A method as recited in claim 1, wherein the ultrasonic SH shear waves are generated in a frequency ranging from 1 MHz to 4 MHz depending upon the tube diameter and wall thickness.

4. A method as recited in claim 3, wherein the frequency of the ultrasonic SH shear waves is adjustable with a range of 1 MHz to 4 MHz as required.

5. A method as recited in claim 4, wherein the predetermined beam angle is determined by the tube size and obtained by adjusting the frequency to obtain the desired beam angle by a relationship of $\sin \Theta = c/2Df$ where:

f=frequency c=shear wave velocity

D=separation between adjacent conductors in an EMAT coil.

\* \* \* \* \*